United States Patent
Stolz

(10) Patent No.: US 8,262,600 B2
(45) Date of Patent: Sep. 11, 2012

(54) DEVICE FOR CARRYING OUT NAIL CORRECTIONS

(76) Inventor: Bernd Stolz, Amberg (DE)

(*) Notice: Subject to any disclaimer, the term of this patent is extended or adjusted under 35 U.S.C. 154(b) by 240 days.

(21) Appl. No.: 12/744,475

(22) PCT Filed: Nov. 13, 2008

(86) PCT No.: PCT/EP2008/009683
§ 371 (c)(1),
(2), (4) Date: May 24, 2010

(87) PCT Pub. No.: WO2009/065533
PCT Pub. Date: May 28, 2009

(65) Prior Publication Data
US 2010/0262058 A1    Oct. 14, 2010

(30) Foreign Application Priority Data
Nov. 23, 2007  (DE) .......................... 10 2007 056 614

(51) Int. Cl.
*A61F 13/00* (2006.01)
(52) U.S. Cl. ............................................ 602/31; 602/30
(58) Field of Classification Search ............. 602/30–31; 132/73, 200, 73.5; 128/893, 894, 892, 888
See application file for complete search history.

(56) References Cited

U.S. PATENT DOCUMENTS

| 132,872 | A | * | 11/1872 | Stedman | 602/31 |
| 2,938,030 | A | * | 5/1960 | Hoffmann et al. | 540/95 |
| 3,032,032 | A | | 5/1962 | Gifford | |
| 5,012,799 | A | * | 5/1991 | Remmen | 602/30 |
| 5,850,837 | A | | 12/1998 | Shiroyama et al. | |
| 2009/0204045 | A1 | * | 8/2009 | Kim | 602/31 |
| 2010/0228173 | A1 | * | 9/2010 | Ishida et al. | 602/31 |

FOREIGN PATENT DOCUMENTS

| BE | 457090 A | 8/1944 |
| CH | 268681 A | 5/1950 |
| DE | 19711923 A1 | 11/1997 |
| DE | 102006018987 A1 | 10/2007 |
| EP | 0282645 A1 | 9/1988 |
| JP | 2003265508 A * | 9/2003 |

* cited by examiner

*Primary Examiner* — Kim M Lewis
(74) *Attorney, Agent, or Firm* — Browdy and Neimark, PLLC

(57) ABSTRACT

A device for carrying out nail corrections, in particular in ingrown nails which are too severely curved, comprises at least one plastics material strip extending in a longitudinal direction. The plastics material strip is rubbery-elastic and longitudinally elastic. At each longitudinal end, it has a hook for engaging around and underneath the nail edge of the toenail to be corrected. The plastics material strip is expandable and, with the hook hooked in, can be adapted with respect to its length to a nail width of the nail to be corrected, so a restoring force due to elasticity brings about an upward force automatically adapted to a degree of curvature of the nail to be corrected.

13 Claims, 1 Drawing Sheet

DEVICE FOR CARRYING OUT NAIL CORRECTIONS

FIELD OF THE INVENTION

The invention is directed at a device for carrying out nail corrections, in particular in the case of an ingrown nail which is too severely curved, comprising at least one plastics material strip extending in a longitudinal direction.

BACKGROUND OF THE INVENTION

A device of this type is known from EP 0 282 645 A1. This previously known correction strip is bonded over its entire area to the upper side of the nail to be corrected, for which purpose it has to be bent following the outer contour of the nail. During this deflection, an elastic restoring force is produced, which acts, in particular, on the toenail edges and lifts them up. A similar device is described in DE 197 11 923 A1, the correction strips disclosed there do not consist of plastics material, but of a super-elastic material, such as, for example, a nickel-titanium alloy.

The disadvantage in these tested devices, which are very effective per se, is that the handling of the rapid adhesives requires a high degree of attention, as, because of their high adhesive force, there is a risk of the fingers of the person handling them sticking together or the adhesive causing damage elsewhere.

Devices made of metal are also already known from DE 10 2006 018 987 A1, for example, and have lateral hooks which in each case engage around and underneath a side edge of the nail to be corrected, an adjustable tensioning force then being applied by means of a type of tensioning screw. The disadvantage in these devices is that when they are worn in shoes, they are experienced as unpleasant and act in a very disruptive manner when pulling socks or stockings on and off. For this reason, devices of this type are often covered with a dressing or a plaster, in particular because of the comparatively voluminous clamping part unit, so the wearing comfort is further impaired, however. Moreover, the structure is relatively complicated, which also makes these known devices expensive.

SUMMARY OF THE INVENTION

Proceeding from this, the invention is based on the object of providing a generic device, which is simple to produce and also to handle, avoids the handling of adhesive and nevertheless has an effectiveness which corresponds to that of the known plastics material strips or is superior thereto.

This object is achieved according to the invention in that the plastics material strip is rubbery-elastic and longitudinally elastic and, at its two longitudinal ends, viewed in the longitudinal direction, has a respective hook to engage around and underneath a nail edge of the nail to be corrected, the plastics material strip being expandable and, when the hook is hooked in, being adaptable with respect to its length to a nail width of the nail to be corrected, so that a restoring force due to elasticity brings about an upward force automatically adapted to a degree of curvature of the nail to be corrected.

To apply a device according to the invention, one of the two end hooks is firstly hooked in underneath the side outer edge of the toenail to be corrected. The plastics material strip is then tensioned and the hook at the other end is hooked in under the opposing toenail edge. In the process, the plastics material strip is expanded and adapted top the nail width. If the nail straightens up again slightly because of the correction device in the course of the treatment time, the expansion of the elastic plastics material strip is reduced, so the restoring force and therefore the upward force become slightly less. The device according to the invention thus adapts automatically to the changed circumstances during the treatment. A manual retensioning or loosening or even an exchange of the correction device for another one is not necessary It becomes clear from the above that the plastics material strip in particular has an undersize compared to the width of the toenail, so a tensioning force and therefore a restoring force is produced on the edges of the toenail by the elastic expansion.

In order to optimise this restoring force or make it adjustable, the plastics material strip may have different lengths and/or different widths. A plurality of plastics material strips of this type may also be placed parallel next to one another.

In each case, a simple application is ensured and the use of adhesive is avoided.

The plastics material strip preferably consists of an elastomer.

The end hooks may, in particular, be glued to the longitudinally elastic plastics material strips. This can be produced easily. Moreover, it is thus, in particular, possible to produce the hooks from a relatively hard, dimensionally stable plastics material, which ensures a firm lasting hold at the edge of the toenail. The plastics material of the hooks is preferably harder and more dimensionally stable than that of the plastics material strip.

In an alternative embodiment it is provided that the plastics material strip and hooks are in one piece or injection-moulded together from plastics material. Thus the hooks and the plastics material strip can preferably be configured as a joint plastics material injection-moulded part, which is produced, for example, by means of a two-component injection moulding method (=2 component method). In this case, a first plastics material is introduced for the rubbery-elastic plastics material strip and a second plastics material is introduced for the hooks into a single injection mould in the course of a joint production process. This takes place simultaneously or successively, but in any case still before the plastics material introduced first has completely hardened. As a result of this favourable production process, a very rigid connection results between the plastics material strip and the hooks. A separate bonding is not then necessary.

In order, in particular in a one-piece configuration, on the one hand, to achieve an adequate holding force of the hooks and, on the other hand, an adequate elasticity of the plastics material strip, the plastics material strip may be provided with material weakenings in the plastics material strip such as, for example, indentations. The plastics material strip may also, however, have material weakenings of this type independently of the production method used and independently of the connection to the hooks, for example to adjust a desired longitudinal elasticity. The longitudinal elasticity can thus be increased.

According to a further preferred configuration, a plurality of rubbery-elastic and longitudinally elastic plastics material strips in each case arranged next to one another perpendicular to the longitudinal direction, in other words, in particular parallel to one another, are provided between the two end hooks. The longitudinal elasticity can also be adjusted thereby. In particular, the upward force can be increased in that the number of plastics material strips arranged in parallel next to one another is increased.

According to a further preferred configuration, the device can be used several times and/or can be disinfected. This saves resources. Moreover, this increases the value of the device to the user.

According to a further preferred configuration, the hooks may be produced from a resilient material. As a result, the device is more flexible to use. Moreover, the user is less affected thereby. Slightly more resilient hooks cause less pain on the nail bed than very hard hooks.

According to further preferred configurations, the hooks in each case have a U-shaped longitudinal cross section with an angular or rounded transition between the U-sides and the U-base or a longitudinal cross section in the form of a ring sector, which extends, in particular, over a peripheral angle of more than 180°. The configuration mentioned first provides a very good hold adapted to the respective circumstances, while the second configuration allows a more flexible application as one and the same device can be used for nails of different thicknesses. By spreading the ring sector, an adaptation to different nail thicknesses is achieved. As a result, the large number of different correction devices to be kept drops.

Further features, advantages and details of the invention emerge from the following description of embodiments with the aid of the drawings.

DESCRIPTION OF THE PREFERRED EMBODIMENT

Figure 1:
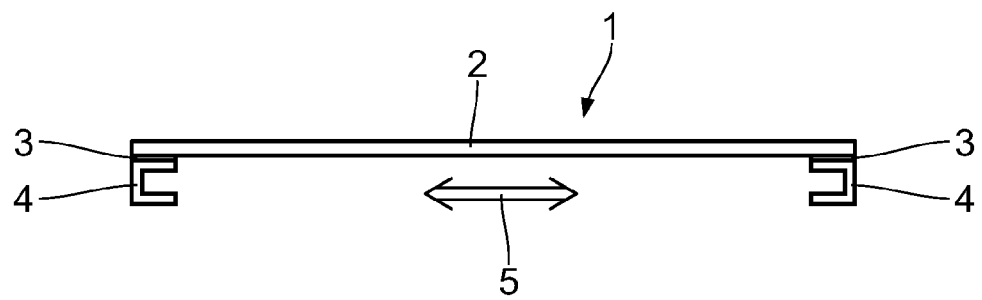
FIG. 1 shows a first embodiment of a device for nail correction with a longitudinally elastic strip and with U-shaped hooks attached on longitudinal ends thereof, in a schematic side view.

Mutually corresponding parts are provided with the same reference numerals in FIGS. 1 to 4.

A nail correction device 1 according to the invention shown in FIG. 1 comprises a central longitudinal strip 2 made of a rubbery-elastic elastomeric plastics material, on the two longitudinal ends of which a U-shaped, inwardly open hook 4 made of a harder plastics material is attached, in each case, by means of a plastics material layer 3. The longitudinally elastic strip 2 extends in a longitudinal direction 5. The strip 2 may be expanded in this longitudinal direction 5, so it is adapted to a width of the nail to be corrected. Because of the expansion, a restoring force which is due to the elasticity is then produced which brings about an upward force on the curved nail to be corrected. Because of the rubbery and longitudinal elasticity of the strip 2, this upward force exerted on the nail is adapted, in particular automatically, to the optionally changing degree of curvature of the nail during the duration of the treatment.

A set of nail correction devices 1 each with a different length may be provided. The strip lengths kept available in this set may be, for example, 12 mm, 14 mm, 16 mm, 18 mm, 20 mm and 22 mm. The nail correction device 1 best suited for the respective application can then be selected. If the nail to be corrected, for example has a nail width of 18 mm, the nail correction device 1 is applied with a comparatively small strip length, in particular of 14 mm or 16 mm. The resulting expansion by 4 mm or 2 mm then brings about the desired upward force. The strip 2 in the applied state is preferably expanded by up to about 5 mm or by up to about 30%, in particular by up to about 15% of its starting length provided in the non-applied state.

Figure 2:
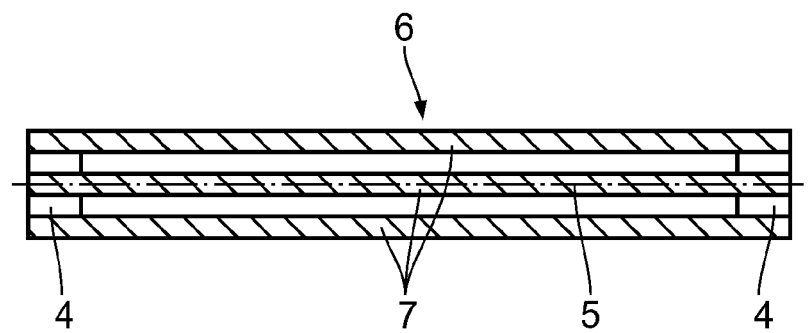
FIG. 2 shows a second embodiment of a device for nail correction with a plurality of longitudinal elastic strips located next to one another, in a schematic plan view.

FIG. 2 shows another embodiment of a nail correction device 6. In contrast to the nail correction device 1 according to FIG. 1, it comprises a total of three in turn rubbery-elastic and longitudinally elastic strips 7 located in parallel next to one another and extending in the longitudinal direction 5, made of a plastics material. The number of three strips 7 is to be understood by way of example. Basically, more or less strips 7 may also be arranged next to one another. The three strips 7 are together connected to one of the hooks 4, in each case, at each longitudinal end. Because of the parallel arrangement of a plurality of strips 7, the longitudinal elasticity and therefore the upward or tensile force on the nail can also be adjusted very precisely and variably within certain limits. Thus, one or more of the strips 7 can be cut through namely in the event of partial treatment progress occurring to thus adjust only a lower upward or tensile force still required for the remaining treatment.

Figure 3:
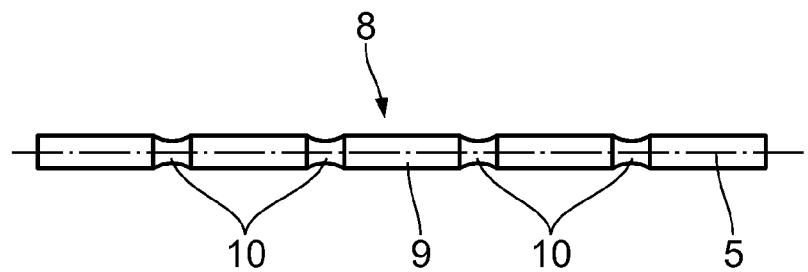
FIG. 3 shows a third embodiment of a device for nail correction with a longitudinally elastic strip provided with material weakenings, in a schematic plan view.

FIG. 3 shows an embodiment of a nail correction device 8, in which a plastics material strip 9 is provided with material weakenings 10. Because of the regions thus formed with a smaller cross sectional area perpendicular to the longitudinal direction 5, the longitudinal elasticity of the plastics material strip 9 can be increased. It is then possible to produce the plastics material strip 9 and the hooks 4 from the same material, and in particular also as a one-piece component, for example as a joint plastics material injection-moulded part.

Figure 4:
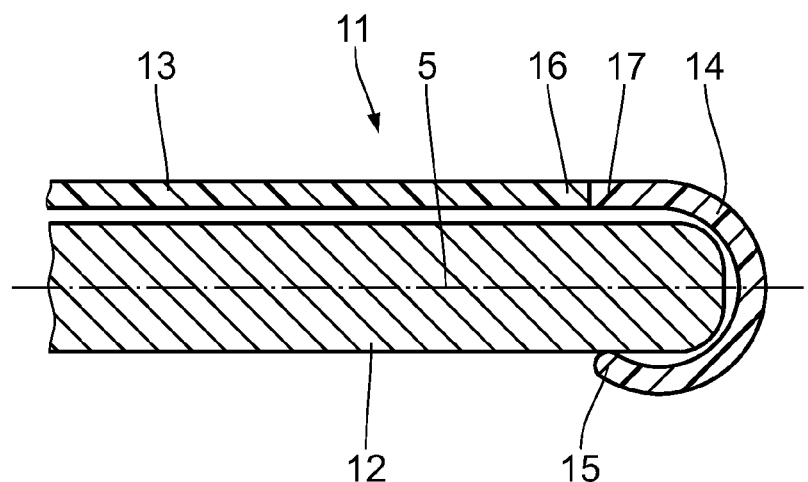
FIG. 4 shows a fourth embodiment of a device for nail correction with a ring sector-shaped hook in a cutout-wise schematic side view and in the applied state.

The cutout according to FIG. 4 shows a further embodiment of a nail correction device 11 in the applied state, i.e. in the state attached to a nail 12 to be corrected. The nail correction device 11 is also composed of a central longitudinally elastic strip 13 and two hooks 14 moulded on to the longitudinal ends of the strip 13. The hooks 14, of which in the cutout according to FIG. 4, only one is shown, consist of plastics material, but from a different plastics material to the strip 13. Compared to the rubbery-elastic strip 13, the hooks 14 are harder, but still elastic to a certain degree.

The hooks 14, in the side view according to FIG. 4 or in a cross sectional plane, which contains the longitudinal direction 5, have an approximately ring sector shape or approximately the shape of an open O. The peripheral angle range moved through by the virtually ring sector-shaped hook 14 is greater than 180°. Because of the certain elasticity or resilient nature of the hooks 14 provided, a free hook end 15 may be bent up and thus a receiving region of the hook 14 adapted to the thickness of the nail 12.

The strip 13 and the hooks 14 are produced by means of a two-component injection-moulding process. They form a joint plastics material injection-moulded part. This produces a rigid, in particular adhesive-free connection between a longitudinal end 16 of the strip and a coupling end 17 of the hook 14. This connection is formed in the embodiment shown in that the end faces of the strip 13 at the strip end 17 and of the hook 14 at the coupling end 17 bluntly abut one another. Because of the two-component production method used, a close material interconnection is established at this coupling point between the two plastics materials of the strip 13 and the hook 14.

The nail correction devices 1, 6, 8 and 11 can be disinfected. Thus, they can be cleaned after use in such a way that they can be used again.

The invention claimed is:

1. A device for carrying out nail corrections, comprising at least one plastics material strip (2; 7; 9; 13) extending in a longitudinal direction (5), wherein the plastics material strip (2; 7; 9; 13) is rubbery-elastic and longitudinally elastic and, at its two longitudinal ends (16), viewed in the longitudinal direction (5), has a respective hook (4; 14) to engage around and underneath a nail edge of the nail (12) to be corrected, the plastics material strip (2; 7; 9; 13) being expandable and, when the hook (4; 14) is hooked in, being adaptable with respect to its length to a nail width of the nail (12) to be corrected, so that a restoring force due to elasticity brings about an upward force automatically adapted to a degree of curvature of the nail (12) to be corrected, and wherein the hooks (4; 14) consist of a plastics material, which is harder and more dimensionally stable than the plastics material of the plastics material strip (2; 7; 9; 13).

2. A device for carrying out nail corrections according to claim 1, wherein the device is adapted for use on an ingrown nail which is too severely curved.

3. A device according to claim 1, wherein the plastics material strip (2; 7; 9; 13) consists of an elastomer.

4. A device according to claim 1, wherein the longitudinally elastic plastics material strip (2; 7) is bonded to the end hook (4).

5. A device according to claim 1, wherein the hooks (14) and the plastics material strip (9; 13) are configured as a joint plastics material injection-moulded part.

6. A device according to claim 1, wherein material weakenings (10) are provided in the plastics material strip (8).

7. A device according to claim 1, wherein a plurality of rubbery-elastic and longitudinally elastic plastics material strips (7) in each case arranged next to one another perpendicular to the longitudinal direction (5) are provided between the two end hooks (4).

8. A device according to claim 1, wherein it can be used several times.

9. A device according to claim 1, wherein it can be disinfected.

10. A device according to claim 1, wherein the hooks (4; 14) consist of a resilient material.

11. A device according to claim 1, wherein the hooks (4) each have a U-shaped longitudinal cross section with one of the group of an angular or a rounded transition between the U-sides and the U-base.

12. A device according to claim 1, wherein the hooks (14) in each case have a longitudinal cross section in the shape of a ring sector.

13. A device according to claim 12, wherein the ring sector of the hook (14) extends over a peripheral angle of more than 180°.

\* \* \* \* \*